US009826948B2

(12) United States Patent
Lee et al.

(10) Patent No.: US 9,826,948 B2
(45) Date of Patent: Nov. 28, 2017

(54) X-RAY DETECTOR AND METHOD OF CONFIGURING THE SAME

(71) Applicant: SAMSUNG ELECTRONICS CO., LTD., Suwon-si (KR)

(72) Inventors: Dong-hun Lee, Hwaseong-si (KR); Jeong-sik Kim, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/751,766

(22) Filed: Jun. 26, 2015

(65) Prior Publication Data

US 2016/0015341 A1    Jan. 21, 2016

(30) Foreign Application Priority Data

Jul. 18, 2014    (KR) .................. 10-2014-0091321

(51) Int. Cl.
*G01T 1/17*    (2006.01)
*A61B 6/00*    (2006.01)
*G01T 1/161*   (2006.01)

(52) U.S. Cl.
CPC .............. *A61B 6/4405* (2013.01); *A61B 6/42* (2013.01); *A61B 6/4411* (2013.01); *A61B 6/4494* (2013.01); *A61B 6/548* (2013.01); *A61B 6/566* (2013.01); *G01T 1/161* (2013.01); *G01T 1/17* (2013.01)

(58) Field of Classification Search
CPC ................................. G01T 1/17; G01T 1/161
See application file for complete search history.

(56) References Cited

U.S. PATENT DOCUMENTS

| 2007/0116180 A1 | 5/2007 | Omernick et al. |
| 2011/0110494 A1 | 5/2011 | Lee |
| 2012/0045991 A1* | 2/2012 | Nonaka ................... H04W 4/00 455/41.2 |
| 2012/0195407 A1 | 8/2012 | Nenoki et al. |
| 2013/0329860 A1 | 12/2013 | Nonaka |

FOREIGN PATENT DOCUMENTS

EP    2564782 A1    3/2013

OTHER PUBLICATIONS

Communication dated Nov. 25, 2015, from the European Patent Office in counterpart European Application No. 15174792.0.

* cited by examiner

*Primary Examiner* — Edwin Gunberg
(74) *Attorney, Agent, or Firm* — Sughrue Mion, PLLC (57) ABSTRACT

Provided is an X-ray detector including: a data transceiver configured to wirelessly receive identification (ID) information relating to a central controller from the central controller when the X-ray detector is in a sharing mode in which the X-ray detector exchanges certain data with the central controller; and a processor configured to perform a configuration based on the received ID information.

24 Claims, 9 Drawing Sheets

| | work staion ID | CONNECTION TIME |
|---|---|---|
| 1 | 192.168.197.30 | 2014.6.19 PM2:30 |
| 2 | 192.168.197.32 | 2014.6.19 PM4:00 |
| 3 | 192.168.197.30 | 2014.6.23 AM11:00 |

X-RAY DETECTOR AND METHOD OF CONFIGURING THE SAME

CROSS-REFERENCE TO RELATED APPLICATION

This application claims priority from Korean Patent Application No. 10-2014-0091321, filed on Jul. 18, 2014, in the Korean Intellectual Property Office, the disclosure of which is incorporated herein by reference in its entirety.

BACKGROUND

1. Field

One or more exemplary embodiments relate to sharing and configuration of an X-ray detector used in an X-ray imaging apparatus, and more particularly, to a method for automatically connecting and configuring a wireless digital X-ray detector.

2. Description of the Related Art

Various types of X-ray detectors are being used in X-ray imaging apparatuses as radiographic apparatuses for medical applications.

As the number of X-ray detectors that are available in an X-ray imaging room increases, it is critical for a workstation within the X-ray imaging room to recognize the X-ray detectors and to suitably configure the X-ray detectors for operation with the workstation. In this case, a workstation is a control device that controls an X-ray detector to perform X-ray imaging and is also called a "central control unit" and/or a "central controller".

When each of the X-ray detectors is connected to the workstation, it is necessary to configure the X-ray detectors to operate appropriately with the workstation.

As a wide variety of types of X-ray detectors have been available in recent years, a workstation needs to connect to such a wide variety of types of X-ray detectors individually. If each of the X-ray detectors is connected to the workstation, a large amount of time and user manipulation is required for the workstation to repeat a process which includes individually checking whether an X-ray detector is registered and registering the X-ray detector. Furthermore, due to the widespread use of wireless digital X-ray detectors, X-ray detectors may not only be used for a single workstation but also be shared among a plurality of workstations. Thus, each time an X-ray detector is connected to a workstation, it becomes a burdensome process to configure the X-ray detector to operate with the workstation. Thus, there is still a need to simplify the process.

SUMMARY

One or more exemplary embodiments include an X-ray detector and a method of configuring the same that enable quick registration of the X-ray detector with a workstation by minimizing user manipulation.

Additional aspects will be set forth in part in the description which follows and, in part, will be apparent from the description, or may be learned by practice of the presented exemplary embodiments.

According to one or more exemplary embodiments, an X-ray detector that wirelessly connects to a central controller includes: a data transceiver configured to wirelessly receive, from the central controller, identification (ID) information that relates to the central controller when the X-ray detector is in a sharing mode in which the X-ray detector exchanges predetermined data with the central controller; and a processor configured to perform a configuration based on the received ID information.

The X-ray detector may be configured to automatically connect to the central controller in a wireless manner.

The X-ray detector may further include a memory configured to store connection history information that includes information relating to a history of connections of the central controller to the X-ray detector, and the processor may be further configured to perform the configuration of the central control unit based on the received ID information and the stored connection history information.

The processor may be further configured to determine whether configuration data used for the configuration of the central controller (hereinafter, referred to as 'configuration data for the central controller') is the same as configuration data used for the configuration performed by the processor based on the ID information and the connection history information.

The processor may be further configured to determine, based on the connection history information, whether the central controller that transmits the ID information is identical to a second central controller which connected last to the X-ray detector, and, if the central controller that transmits the ID information is different from the second central controller which connected last to the X-ray detector, to change a service set identifier (SSID) of the X-ray detector to be the same as an SSID of the central controller that transmits the ID information.

The memory may be further configured to store X-ray detector configuration data that is used for a configuration of the X-ray detector, and if the configuration data for the central controller is different from the X-ray detector configuration data, the data transceiver may be further configured transmit the stored X-ray detector configuration data to the central controller.

The X-ray detector configuration data may include at least one from among calibration data, a detection parameter, an Internet Protocol (IP) address, an SSID, and a media access control (MAC) address of the X-ray detector.

The connection history information may include at least one piece of ID information that relates to a central controller that was previously connected to the X-ray detector and at least one piece of time information that indicates at least one time when the central controller was previously connected to the X-ray detector.

The ID information may include at least one from among an IP address, a serial number, an SSID, and a MAC address of the central controller.

The ID information may be broadcast by the central controller.

The X-ray detector may be further configured to wirelessly connect to the central controller that transmits the ID information when the X-ray detector is in a sharing mode.

The X-ray detector may further include a user input receiver via which the sharing mode is initiated when a user input is received via the user input receiver.

The sharing mode may be initiated when the data transceiver receives a command input via the central controller.

The X-ray detector may further include a display configured to display data being transmitted and/or received by the data transceiver, and the display may be further configured to display a user interface screen indicating a status of a transmission of configuration data used for the configuration performed by the processor to the central controller.

According to one or more exemplary embodiments, an X-ray image processing system includes the X-ray detector and a central controller.

The central controller may be located within an X-ray imaging room.

The central controller may be included in a mobile X-ray system.

According to one or more exemplary embodiments, a method for using an X-ray detector includes: wirelessly receiving, from a central controller, ID information that relates to the central controller when the X-ray detector is in a sharing mode in which the X-ray detector exchanges certain data with the central controller; and performing a configuration based on the received ID information.

The performing the configuration may include the X-ray detector automatically connecting to the central controller in a wireless manner.

The performing the configuration may further include determining whether configuration data used for the configuration of the central controller (hereinafter, referred to as the 'configuration data for the central control unit') is the same as configuration data used for the configuration performed by the X-ray detector based on the ID information and the connection history information.

The performing the configuration may include: determining, based on the connection history information, whether the central controller that transmits the ID information is identical to a second central controller which connected last to the X-ray detector; and changing an SSID of the X-ray detector to be the same as an SSID of the central controller that transmits the ID information if the central controller that transmits the ID information is different from the second central controller which connected last to the X-ray detector.

The method may further include storing X-ray detector configuration data that is used for a configuration of the X-ray detector in the memory of the X-ray detector, and the performing the configuration may further include, if the configuration data for the central controller is different from the X-ray detector configuration data, transmitting the stored X-ray detector configuration data to the central controller.

The X-ray detector configuration data for the X-ray detector may include at least one from among calibration data, a detection parameter, an IP address, an SSID, and a MAC address of the X-ray detector.

The connection history information may include at least one piece of ID information of a central controller that was previously connected to the X-ray detector and at least one piece of time information indicating at least one time when the central controller was previously connected to the X-ray detector.

The ID information may include at least one selected from an IP address, a serial number, an SSID, and a MAC address of the central controller.

In the X-ray detector automatically connecting to the central controller in a wireless manner, the X-ray detector may connect wirelessly to the central controller that transmits the ID information when the X-ray detector is in a sharing mode.

The sharing mode may be initiated when a user input receiver of the X-ray detector receives a user input.

A data transceiver of the X-ray detector may receive a command input via the central controller in order to initiate the sharing mode.

The performing the configuration may include displaying a status of a transmission of configuration data used for the configuration performed by the X-ray detector to the central controller.

According to an exemplary embodiment, checking a list of X-ray detectors to which a workstation is able to connect is unnecessary before the workstation connects to each of the X-ray detectors. Thus, an automatic connection between a new X-ray detector and the workstation is allowed.

Furthermore, according to an exemplary embodiment, it is not necessary for an X-ray detector to request a configuration from a workstation in order to perform configuration of the X-ray detector. In other words, the X-ray detector may be automatically configured without needing to receive calibration data from the workstation.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

The attached drawings for illustrating exemplary embodiments are referred to in order to gain a sufficient understanding of the present inventive concept, the merits thereof, and the objectives accomplished by the implementation of the present inventive concept. The present inventive concept may, however, be embodied in many different forms and should not be construed as being limited to the exemplary embodiments set forth herein; rather, these exemplary embodiments are provided such that this disclosure will be thorough and complete, and will fully convey the present inventive concept to one of ordinary skill in the art.

Hereinafter, the terms used in the specification will be briefly described, and then the exemplary embodiments will be described in detail.

The terms used in this specification are those general terms currently widely used in the art in consideration of functions regarding the exemplary embodiments, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the exemplary embodiments.

Throughout the specification, an "image" may denote multi-dimensional data composed of discrete image elements (for example, pixels in a two-dimensional image and voxels in a three-dimensional image). For example, an image may include medical images of an object acquired by an X-ray apparatus, a computed tomography (CT) apparatus, a magnetic resonance imaging (MRI) apparatus, an ultrasound wave apparatus, and other medical image systems.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. The object may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a technician who repairs a medical apparatus.

Figure 1:
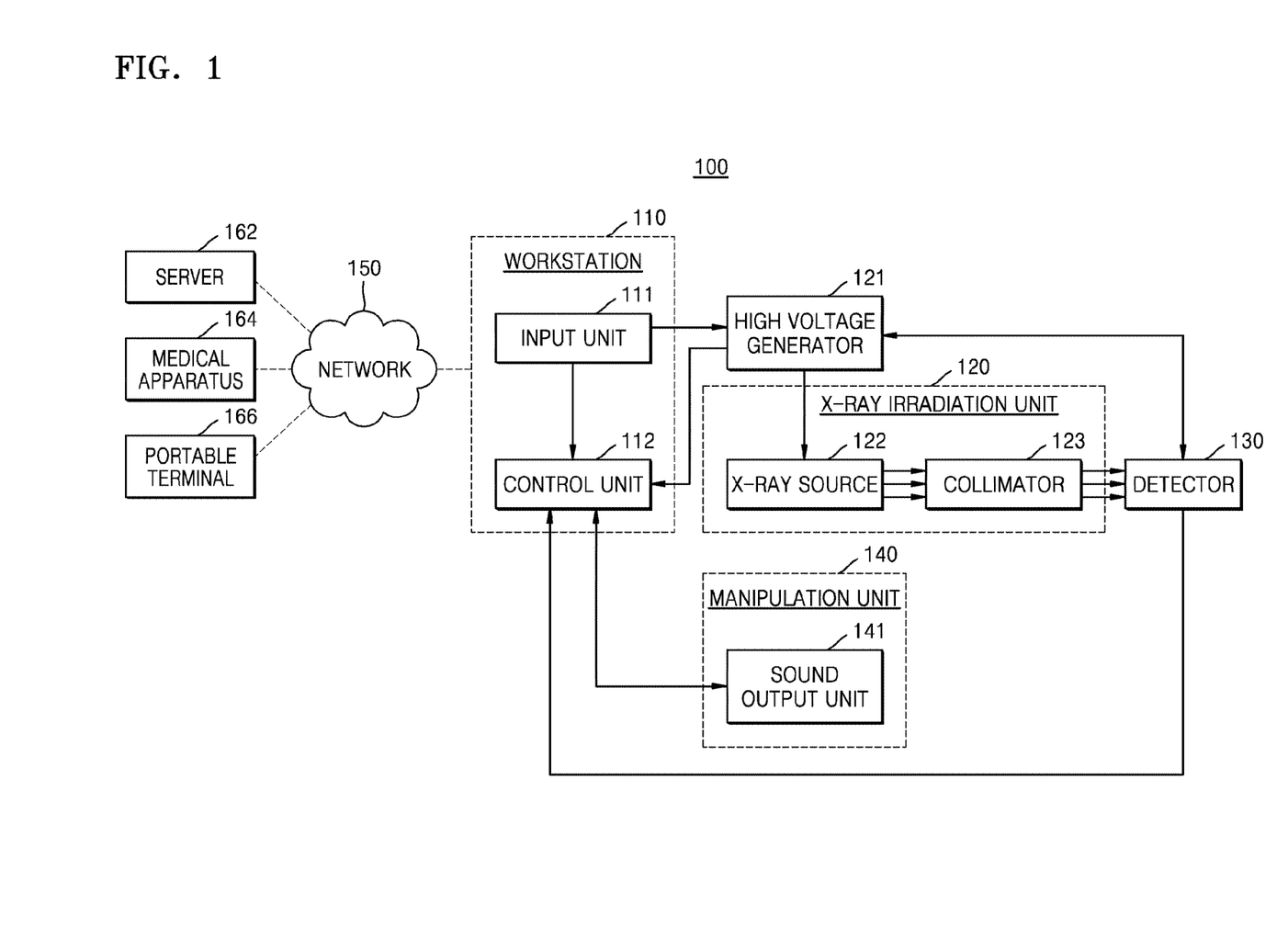
FIG. 1 is a block diagram of a general X-ray apparatus.

FIG. 1 is a block diagram of an X-ray apparatus 100. The X-ray apparatus 100 shown in FIG. 1 may be a fixed-type X-ray apparatus or a mobile X-ray apparatus.

Referring to FIG. 1, the X-ray apparatus 100 includes a workstation 110, an X-ray irradiation unit (also referred to herein as an "X-ray irradiator") 120, a high voltage generator 121, and a detector 130.

The workstation 110 includes an input unit (also referred to herein as an "input device") 111 through which a user may input commands for manipulating the X-ray apparatus 100 including an X-ray irradiation, and a control unit (also referred to herein as a "controller") 112 which is configured for controlling overall operations of the X-ray apparatus 100.

The high voltage generator 121 generates a high voltage for generating X-rays, and applies the high voltage to an X-ray source 122.

The X-ray irradiation unit 120 includes the X-ray source 122 which is configured for receiving the high voltage applied from the high voltage generator 121 in order to generate and irradiate the X-ray, and a collimator 123 which is configured for guiding a path of the X-ray irradiated from the X-ray source 122.

The detector 130 detects the X-ray that is irradiated from the X-ray irradiation unit 120 and has propagated through the object.

Further, the X-ray apparatus 100 may further include a manipulation unit (also referred to herein as a "manipulator") 140 which includes a sound output unit (also referred to herein as a "sound output device") 141 which is configured outputting sound representing information relating to photographing operation such as the X-ray irradiation under a control of the control unit 112. The sound output unit 141 may include a speaker.

The workstation 110, the X-ray irradiation unit 120, the high voltage generator 121, and the detector 130 may be connected to each other via wires or wirelessly. If they are connected to each other wirelessly, a device (not shown) that is configured for synchronizing clocks with each other may be further included.

The input unit 111 may include any of a keyboard, a mouse, a touch screen, a voice recognizer, a fingerprint recognizer, an iris recognizer, and the like well-known in the art. The user may input a command for irradiating the X-ray via the input unit 111, and to do this, the input unit 111 may include a switch for inputting the command. The switch may be configured so that an irradiation command for irradiating the X-ray may be input only when the switch is pushed twice.

In particular, when the user pushes the switch, a prepare command (i.e., a prepare signal) for performing a pre-heating operation for X-ray irradiation may be input via the switch, and then, when the user pushes the switch once more, the irradiation command for irradiating the X-ray may be substantially input via the switch. When the user manipulates the switch as described above, the input unit 111 generates signals corresponding to the commands input through the switch manipulation, that is, a prepare signal and an irradiation signal, and outputs the generated signals to the high voltage generator 121, which then generates a high voltage for generating the X-ray.

When the high voltage generator 121 receives the prepare signal output from the input unit 111, the high voltage generator 121 starts a pre-heating operation, and when the pre-heating is finished, the high voltage generator 121 outputs a ready signal to the control unit 121. In addition, the detector 130 also needs to prepare for detecting the X-ray, and thus, when the high voltage generator 121 receives the prepare signal output from the input unit 111, the high voltage generator 121 outputs a prepare signal to the detector 130 at the same time of performing the pre-heating operation, so that the detector 130 may prepare for detecting the X-ray that has propagated through the object. The detector 130 prepares for detecting the X-ray when receiving the prepare signal, and when the preparing for the detection is finished, the detector 130 outputs a ready signal to the high voltage generator 121 and the control unit 112.

When the pre-heating operation of the high voltage generator 121 is finished, the detector 130 is ready for the detecting the X-ray, and the irradiation signal is output from the input unit 111 to the high voltage generator 121, the high voltage generator 121 generates and applies the high voltage to the X-ray source 122, and the X-ray source 122 irradiates the X-ray.

When the irradiation signal is output from the input unit 111, the control unit 112 may output a sound output signal to the sound output unit 141 so that the sound output unit 141 outputs predetermined sound and the object may recognize the irradiation of an X-ray. Further, the sound output unit 141 may output sound representing other information relating to the photographing, in addition to the X-ray irradiation. In FIG. 1, the sound output unit 141 is included in the manipulation unit 140; however, the exemplary embodiments are not limited thereto, and the sound output unit 141 may be located at a different location from the manipulation unit 140. For example, the sound output unit 141 may be included in the workstation 110, or may be located on a wall surface of an examination room in which the X-ray photographing of the object is performed.

The control unit 112 controls locations of the X-ray irradiation unit 120 and the detector 130, a photographing timing, and photographing conditions according to photographing conditions set by the user.

In more detail, the control unit 112 controls the high voltage generator 121 and the detector 130 according to the command input via the input unit 111 so as to control an irradiation timing of the X-ray, an intensity of the X-ray, and an irradiation region of the X-ray. Also, the control unit 112 adjusts the location of the detector 130 according to a predetermined photographing condition, and controls an operation timing of the detector 130.

In addition, the control unit 112 generates a medical image of the object by using image data received from the detector 130. In detail, the control unit 121 receives the image data from the detector 130, and then, generates the medical image of the object by removing noise in the image data, and adjusting a dynamic range and interleaving of the image data.

The X-ray apparatus 100 shown in FIG. 1 may further include an output unit (not shown) for outputting the medical image generated by the control unit 112. The output unit may output information that is necessary for the user to manipulate the X-ray apparatus 100, for example, a user interface (UI), user information, and/or object information. The output unit may include any of a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a three-dimensional (3D) display, a transparent display, and/or other various output devices well known in the art.

The workstation 110 shown in FIG. 1 may further include a communication unit (not shown) (also referred to herein as a "communicator" and/or as a "transceiver") that may be connected to a server 162, a medical apparatus 164, and a portable terminal 166 via a network 150.

The communication unit may be connected to the network 150 via wires or wirelessly to communicate with the external server 162, the external medical apparatus 164, or the external portable terminal 166. The communication unit may transmit or receive data relating to diagnosis of the object via the network 150, and may transmit or receive medical images captured by the other medical apparatus 164, for example, a CT, an MRI, or an X-ray apparatus. Moreover, the communication unit may receive medical history or treatment schedule of an object (e.g., a patient) from the server 162 to diagnose a disease of the object. Also, the communication unit may perform data communication with the portable terminal 166, such as a mobile phone of a doctor or a patient, a personal digital assistant (PDA), or a laptop computer, as well as the server 162 or the medical apparatus 164 in a hospital.

The communication unit may include one or more elements which are configured to facilitate communications with external apparatuses, for example, any of a short distance communication module, a wired communication module, and a wireless communication module.

The short distance communication module is a module for communicating with a device located within a predetermined distance. The short distance communication technology may include any of a wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, the exemplary embodiments are not limited thereto.

The wired communication module is a module for communicating by using an electric signal or an optical signal, and the wired communication technology may be wired communication technology which uses any of a pair cable, a coaxial cable, or an optical fiber cable, and a wired communication technology that is well known in the art.

The wireless communication module may transmit/receive a wireless signal to/from at least one of a base, an external device, and a server in a mobile communication network. Here, the wireless signal may be any of a voice call signal, a video call signal, and/or various types of data according to text/multimedia messages transmission.

The X-ray apparatus 100 shown in FIG. 1 may include any of a plurality of digital signal processors (DSPs), an ultra-small calculator, and a processing circuit for specialized usage (for example, a high speed analog/digital (A/D) conversion, a high speed Fourier transformation, an array process, etc.).

In addition, the communication between the workstation 110 and the X-ray generator 120, the workstation 110 and the high voltage generator 121, and the workstation 110 and the detector 130 may use a high speed digital interface, such as low voltage differential signaling (LVDS), asynchronous serial communication, such as universal asynchronous receiver transmitter (UART), synchronous serial communication, or a low latency network protocol, such as a controller area network (CAN), and other various communication methods that are well known in the art may be used.

In order that the workstation 110 of the X-ray apparatus 100 is able to connect to and operate with the detector 130, a configuration of the workstation 110 must correspond to a configuration of the detector 130.

Configuration that is performed before commencement of X-ray imaging by the X-ray apparatus 100 will be described in more detail below.

Furthermore, as described above, the workstation 110 is a control device that controls an X-ray detector to perform X-ray imaging and is also hereinafter referred to as a "central control unit" and/or as a "central controller". For convenience of explanation, the central control unit 110 used herein also has the same meaning as the workstation 110.

Figure 2:
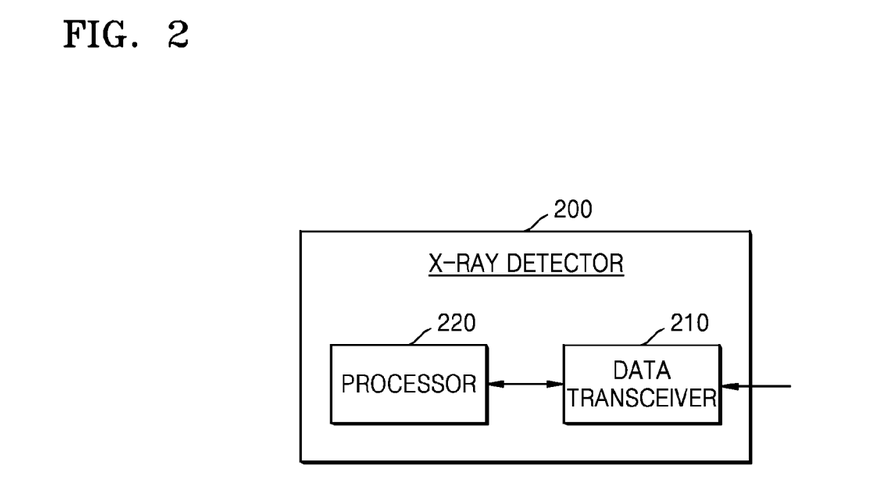
FIG. 2 is a diagram of a structure of an X-ray detector, according to an exemplary embodiment.

FIG. 2 is a diagram of a structure of an X-ray detector 200, according to an exemplary embodiment.

The X-ray detector 200 according to the present exemplary embodiment may detect an X-ray that is emitted by the X-ray irradiation unit 120 and passes through an object. The X-ray detector 200 may include the detector 130 shown in FIG. 1.

Referring to FIG. 2, the X-ray detector 200 may include a data transceiver 210 and a processor 220.

The data transceiver 210 may transmit and/or receive data wirelessly. When the X-ray detector 200 is in a sharing mode in which the data transceiver 210 exchanges certain data with a central control unit, the data transceiver 210 may wirelessly receive identification (ID) information relating to the central control unit from the central control unit.

The processor 220 may perform a configuration based on the received ID information.

The data transceiver 210 may wirelessly receive ID information of the workstation (hereinafter, referred to as the central control unit) 110 from the central control unit 110 shown in FIG. 1. In this case, ID information refers to unique information that relates to the central control unit 110, which is usable to individually identify the central control unit 110. Furthermore, the ID information received from the central control unit 110 may include, but is not limited to, any of an Internet Protocol (IP) address, a serial number, a service set identifier (SSID), and a media access control (MAC) address of the central control unit 110.

An IP address is address information that can identify an address where data is transmitted so that an X-ray detector may recognize a central control unit. The IP address may be a unique ID number assigned to individual central control units. A serial number may be a unique ID number assigned to each central control unit when a central control unit is manufactured. A MAC address may also be a unique ID number assigned to each central control unit so that an X-ray detector may recognize a particular central control unit.

An SSID is an identifier that is required for an X-ray detector and a particular central control unit to access each other. A unique SSID may be assigned to each central control unit. Each time an X-ray detector is connected to a central control unit, the X-ray detector may change its SSID to be the same as a unique SSID of the central control unit.

A 'central control unit' that will be described below may correspond to the central control unit 110 in the X-ray apparatus 100 of FIG. 1.

The X-ray detector 200 of FIG. 2 may be a wireless X-ray detector or a wireless digital X-ray detector that connects wirelessly to a central control unit. Furthermore, the X-ray detector 200 may correspond to the detector 130 in the X-ray apparatus 100 described with reference to FIG. 1 and may configure the detector 130.

Alternatively, as described above, the X-ray detector 200 may include the detector 130 shown in FIG. 1.

The data transceiver 210 of the X-ray detector 200 may exchange data with the central control unit 110 in the X-ray apparatus 100.

An example where the X-ray detector 200 is wirelessly connected to a central control unit for operation thereof will now be described. However, exemplary embodiments are not limited thereto, and the X-ray detector 200 may be connected by wire to the central control unit for operation thereof.

Furthermore, the X-ray detector 200 is not wirelessly connectable to an arbitrary central control unit. When both the X-ray detector 200 and the central control unit enter a 'sharing mode', the X-ray detector 200 may connect wirelessly to the central control unit.

A 'sharing mode' refers to a state in which certain data can be exchanged between an X-ray detector and a central control unit. When an X-ray detector that is in a sharing mode recognizes a central control unit that is in a sharing mode, the X-ray detector may automatically connect to the central control unit in a wireless manner. In this aspect, if the X-ray detector and the central control unit are both set to a sharing mode, the X-ray detector and the central control unit may automatically connect to each other in a wireless manner.

In detail, when the central control unit is in a sharing mode, the central control unit may broadcast ID information that relates to the central control unit. The broadcast ID information may be received by the data transceiver 210 of the X-ray detector 200. The central control unit may broadcast or multicast the ID information of the central control unit, but exemplary embodiments are not limited thereto.

According to an exemplary embodiment, the X-ray detector 200 that is set to a sharing mode may receive ID information that is broadcast or multicast by the central control unit. When the X-ray detector 200 receives the ID information of the central control unit, the X-ray detector 200 may determine that the central control unit is set to a sharing mode. If the X-ray detector 200 recognizes the central control unit, the X-ray detector 200 may automatically connect to the central control unit in a wireless manner.

For example, the X-ray detector 200 that is in a sharing mode may receive an SSID of the central control unit that is in a sharing mode. Then, if an SSID of the X-ray detector is changed to the same SSID of the central control unit based on the received SSID, the X-ray detector 200 and the central control unit may automatically connect to each other.

Furthermore, the user may both set the X-ray detector 200 and the central control unit to a sharing mode, or the central control unit or the X-ray detector 200 itself may be set to a sharing mode.

The X-ray detector 200 may be disposed inside an X-ray imaging room (not shown). In this case, if the X-ray detector 200 and a central control unit located within the X-ray imaging room are both in a sharing mode, the X-ray detector 200 may connect wirelessly to the central control unit.

An example where an X-ray detector is located within an X-ray imaging room (not shown) will be described in more detail below with reference to FIG. 5.

Figure 3:
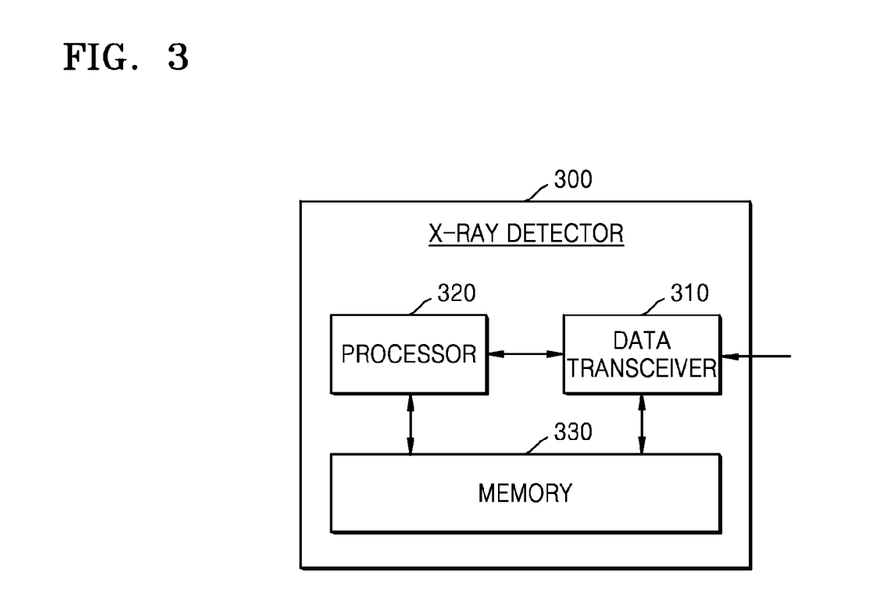
FIG. 3 is a diagram of a structure of an X-ray detector, according to another exemplary embodiment.

FIG. 3 is a diagram of a structure of an X-ray detector 300, according to another exemplary embodiment.

Referring to FIG. 3, the X-ray detector 300 according to the present exemplary embodiment includes a data transceiver 310, a processor 320, and a memory 330. Since the data transceiver 310 and the processor 320 respectively correspond to the data transceiver 210 and the processor 220, repeated descriptions thereof are omitted.

As described above with reference to FIG. 2, the X-ray detector 300 may be a wireless X-ray detector or a wireless digital X-ray detector that can connect wirelessly to a central control unit. Furthermore, the X-ray detector 300 may be included in the X-ray apparatus 100 described with reference to FIG. 1.

In detail, if the X-ray detector 300 is included in the X-ray apparatus 100, the X-ray detector 300 may correspond to the detector 130 shown in FIG. 1 and configure the detector 130. In this case, the data transceiver 310 of the X-ray detector 300 may exchange data with the central control unit 110 in the X-ray apparatus 100 of FIG. 1.

The memory 330 may store connection history information that includes information relating to a history of connections of a central control unit (not shown) to the X-ray detector 300. The processor 320 may configure the central control unit based on ID information of the central control unit and the connection history information.

The connection history information stored in the memory 330 may include at least one piece of ID information that relates to a central control unit that was previously connected to the X-ray detector 300 and at least one piece of time information indicating at least one time and/or at least one date when the central control unit was previously connected to the X-ray detector 300.

The memory 330 may also store configuration data used for performing a configuration of the X-ray detector 300. The configuration data may include at least one selected from calibration data, a detection parameter, an IP address, an SSID, and a MAC address of the X-ray detector 300.

In this case, calibration data may include a set of unique calibration values for each X-ray detector and is required by the central control unit to process X-ray data detected and acquired by the X-ray detector.

A detection parameter may be a set of parameters used by an X-ray detector to detect an image. For example, the detection parameter may include any of information about a size of an X-ray image, information about a model of the X-ray detector, etc.

An IP address is address information that can identify an address where data is transmitted so that a central control unit may recognize an X-ray detector. The IP address may include a unique ID number assigned to individual central control units. A MAC address may also be a unique ID number assigned to each central control unit so that an X-ray detector may recognize a central control unit.

An SSID is an identifier required for an X-ray detector to connect to a particular central control unit. A unique SSID may be assigned to each central control unit. The X-ray detector may change its SSID to be the same as a unique SSID of the central control unit.

The memory 330 may further store a version of configuration data used for performing a configuration of the X-ray detector 300 and information related to a central control unit that was previously connected to the X-ray detector 300.

Although FIG. 3 shows that the memory 330 is included in the X-ray detector 300, the memory 330 may be disposed outside of the X-ray detector 300. Furthermore, the memory 330 may be a flash memory.

Figure 4:
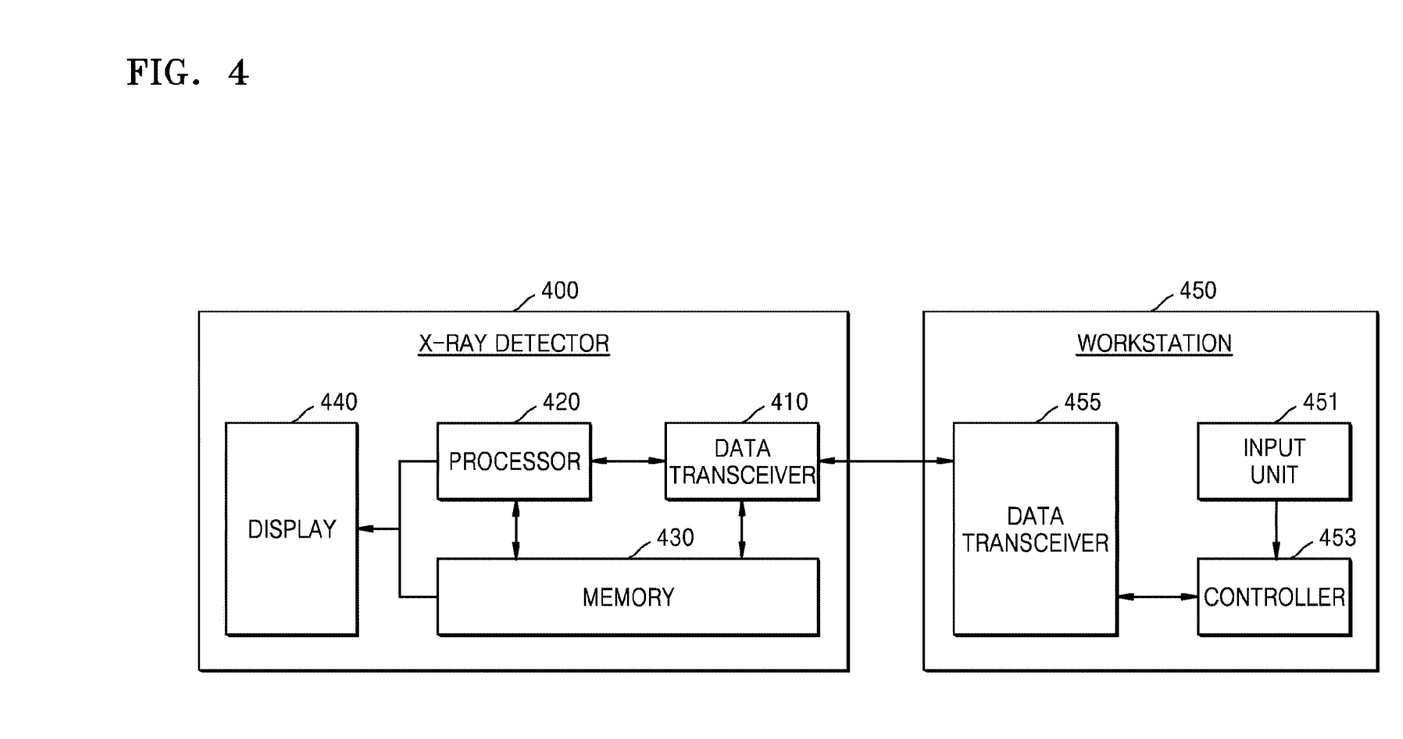
FIG. 4 is a diagram which illustrates a connection of an X-ray detector to a workstation for operation thereof, according to an exemplary embodiment.

FIG. 4 is a diagram which illustrates a connection of an X-ray detector 400 to a workstation 450 for operation thereof, according to an exemplary embodiment.

Referring to FIG. 4, the X-ray detector 400 includes a data transceiver 410, a processor 420, a memory 430, and a display 440. Since the data transceiver 410, the processor 420, and the memory 430 respectively correspond to the data transceiver 310, the processor 320, and the memory 330, repeated descriptions thereof are omitted.

The X-ray detector 400 may be a wireless X-ray detector or a wireless digital X-ray detector that can connect wirelessly to the workstation 450. Furthermore, as described above with reference to FIG. 3, the X-ray detector 400 may be included in the X-ray apparatus 100 described with reference to FIG. 1. In detail, if the X-ray detector 400 is included in the X-ray apparatus 100, the X-ray detector 400 may correspond to the detector 130 shown in FIG. 1.

The display 440 may display data being transmitted and/or received by the data transceiver 410. The display 440 may also display a status of a transmission of configuration data used for a configuration of the X-ray detector 400 (hereinafter, having the same meaning as 'configuration data for the X-ray detector 400' and/or "X-ray detector configuration data") to the workstation 450. Alternatively, if the display 440 does not need to display a status of a transmission of data with respect to the X-ray detector 400, the display 440 may not display the status of data transmission.

Despite not completing a transmission of configuration data for the X-ray detector 400 to the workstation 450, a connection between the X-ray detector 400 and the workstation 450 may be disconnected. When the X-ray detector 400 reconnects to the workstation 450, the processor 420 of the X-ray detector 400 may control a retransmission of the configuration data for which transmission was not previously completed.

The workstation 450 includes an input unit 451, a controller 453, and a data transceiver 455.

Furthermore, the workstation 450 may be included in the X-ray apparatus 100 as described above with reference to FIG. 1. In detail, if the workstation 450 is included in the X-ray apparatus 100, the workstation 450 may correspond to the central control unit 110 shown in FIG. 1. In this case, the input unit 451 and the controller 453 shown in FIG. 4 may respectively correspond to the input unit 111 and the control unit 112 of the central control unit 110.

The workstation 450 may further include a display (not shown). The display may display data being transmitted and/or received by the data transceiver 455. Furthermore, like the display 440 of the X-ray detector 400, the display may display a status of a transmission of configuration data for the X-ray detector 400 to the workstation 450.

When the workstation 450 is entering a sharing mode, the workstation 450 may automatically connect to the X-ray detector 400.

In a sharing mode, the controller 453 of the workstation 450 may control the data transceiver 455 to broadcast ID information of the workstation 450. The broadcasted ID information may be received by the data transceiver 410 of the X-ray detector 400. The data transceiver 455 of the workstation 450 may broadcast or multicast the ID information, but exemplary embodiments are not limited thereto.

When the X-ray detector 400 is in a sharing mode, the X-ray detector 400 may recognize the workstation 450 upon receipt of the ID information of the workstation 450. Thus, the X-ray detector 450 may automatically connect to the workstation 450 that transmits the ID information.

The ID information of the workstation 450 may include, but is not limited to, at least one selected from among an IP address, a serial number, an SSID, and a MAC address.

According to an exemplary embodiment, the X-ray detector 400 that is in a sharing mode may receive an SSID of the workstation 450 that is in a sharing mode. Then, if an SSID of the X-ray detector 400 is changed to be the same as the SSID of the workstation 450 based on the received SSID, the X-ray detector 400 and the workstation 450 may automatically connect to each other.

A sharing mode of the X-ray detector 400 may be initiated when a user input receiver (not shown) receives a user input. The user input receiver may receive a user input via a pressing of buttons or a touch, but the user input is not limited thereto. The sharing mode of the X-ray detector 400 may be initiated when the data transceiver 410 receives a command from the workstation 450.

Using the X-ray detector 400 and the workstation 450 shown in FIG. 4 may eliminate the need to check a list of X-ray detectors to which the workstation 450 is able to connect before the workstation 450 connects to the X-ray detector 400. Thus, after the X-ray detector 400 receives ID information of the workstation 450, the X-ray detector 400 may automatically connect with the workstation 450. Likewise, if the X-ray detector 400 is a new X-ray detector, the X-ray detector 400 and the workstation 450 may automatically connect to each other after the X-ray detector 400 receives ID information of the workstation 450.

Figure 5:
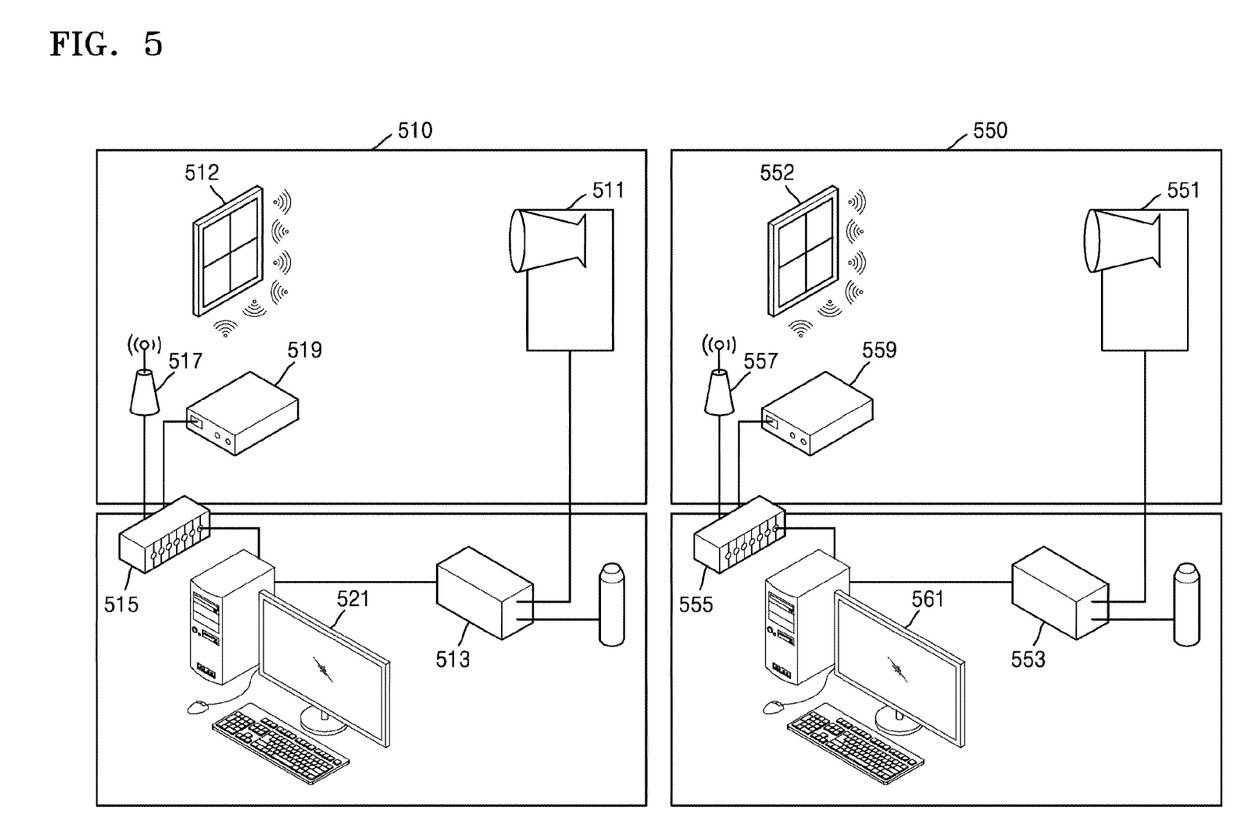
FIG. 5 illustrates structures of two X-ray imaging rooms in relation to an exemplary embodiment.

FIG. 5 illustrates structures of two X-ray imaging rooms A and B 510 and 550 in relation to an exemplary embodiment.

Referring to FIG. 5, the X-ray imaging room A 510 may have an X-ray detector 512 which is configured for detecting an X-ray that is emitted by an X-ray irradiation unit 511, a switch 513, a local area network (LAN) switching hub 515, a wireless access point (WAP) 517, a power supply unit 519, and a workstation 521. In this case, the X-ray detector 512 and the workstation 521 respectively correspond to the X-ray detector 400 and the workstation 450 described with reference to FIG. 4.

The switch 513 may control X-rays emitted by the X-ray irradiation unit 511. The switch 513 may also be configured to receive a user input. For example, X-rays may be emitted when a user presses a button. The LAN switching hub 515 and the WAP 517 are used to relay data received from the X-ray detector 512 to the workstation 521. The power supply unit 519 may supply power to the LAN switching hub 515 and the WAP 517.

Like the X-ray imaging room A 510, the X-ray imaging room B 550 may have an X-ray detector 552 which is configured for detecting an X-ray emitted by an X-ray irradiation unit 551, a switch 553, a LAN switching hub 555, a WAP 557, a power supply unit 559, and a workstation 561.

Since the X-ray irradiation unit 551, the X-ray detector 552, the switch 553, the LAN switching hub 555, the WAP 557, the power supply unit 559, and the workstation 561 respectively correspond to the X-ray irradiation unit 511, the X-ray detector 512, the switch 513, the LAN switching hub 515, the WAP 517, the power supply unit 519, and the workstation 521, detailed descriptions thereof are omitted.

The X-ray detector 200, 300, or 400 described with reference to FIGS. 2, 3, and 4 may be disposed within the X-ray imaging room A 510. If an X-ray detector (not shown) and the workstation 521 are both in a sharing mode, the X-ray detector may perform wireless data communication with the workstation 521.

According to an exemplary embodiment, after the X-ray detector 512 is used in the X-ray imaging room A 510, the X-ray detector 512 may be moved from the X-ray imaging room 510 to the X-ray imaging room B 550. When the X-ray detector 512 is moved to the X-ray imaging room B 550 and the X-ray detector 512 and the workstation 561 in the X-ray imaging room B 550 are both in a sharing mode, the X-ray detector 512 may perform wireless data communication with the workstation 561.

Although FIG. 5 shows that the X-ray detectors 512 and 552 are respectively located within the X-ray imaging rooms A and B 510 and 550, they may be included in a mobile X-ray image processing system.

Figure 6A:
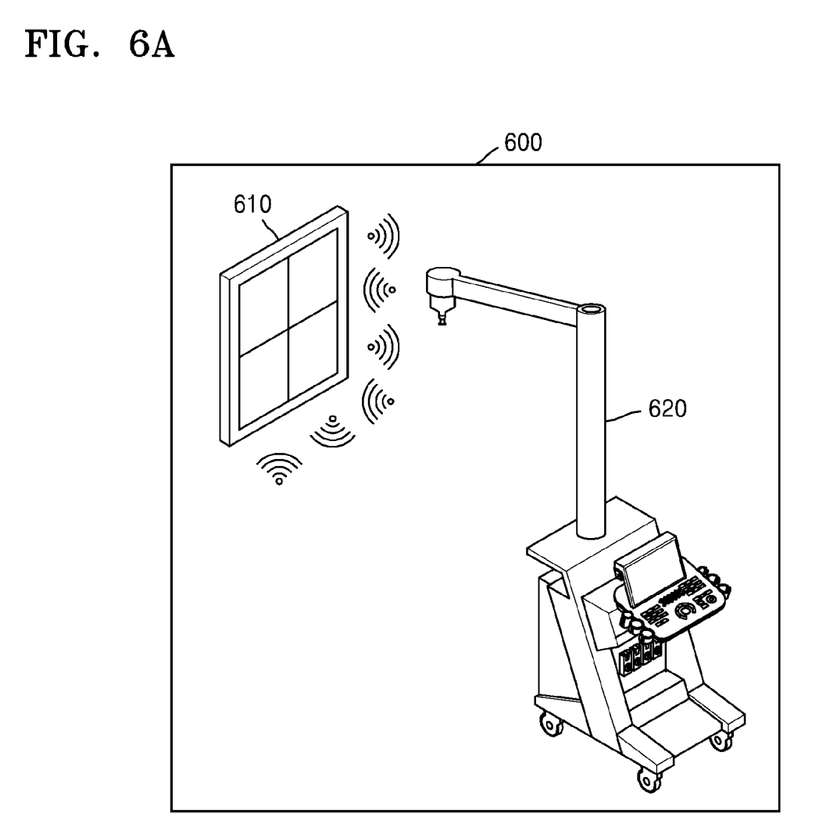
FIG. 6A illustrates an X-ray image processing system, and in particular, a mobile X-ray image processing system, according to an exemplary embodiment.

FIG. 6A illustrates an X-ray image processing system, and in particular, a mobile X-ray image processing system 600, according to an exemplary embodiment.

Referring to FIG. 6A, the mobile X-ray image processing system 600 may include a wireless X-ray detector 610 and a mobile X-ray processor 620.

The X-ray detectors 200, 300, and 400 described above with reference to FIGS. 2, 3, and 4 may correspond to the wireless X-ray detector 610 included in the mobile X-ray image processing system 600.

Furthermore, the workstation 450 described with reference to FIG. 4 may be included in the mobile X-ray image processing system 600, and in particular, in the mobile X-ray processor 620.

The mobile X-ray image processing system 600 of FIG. 6A may be configured to perform X-ray imaging regardless of location.

Figure 6B:
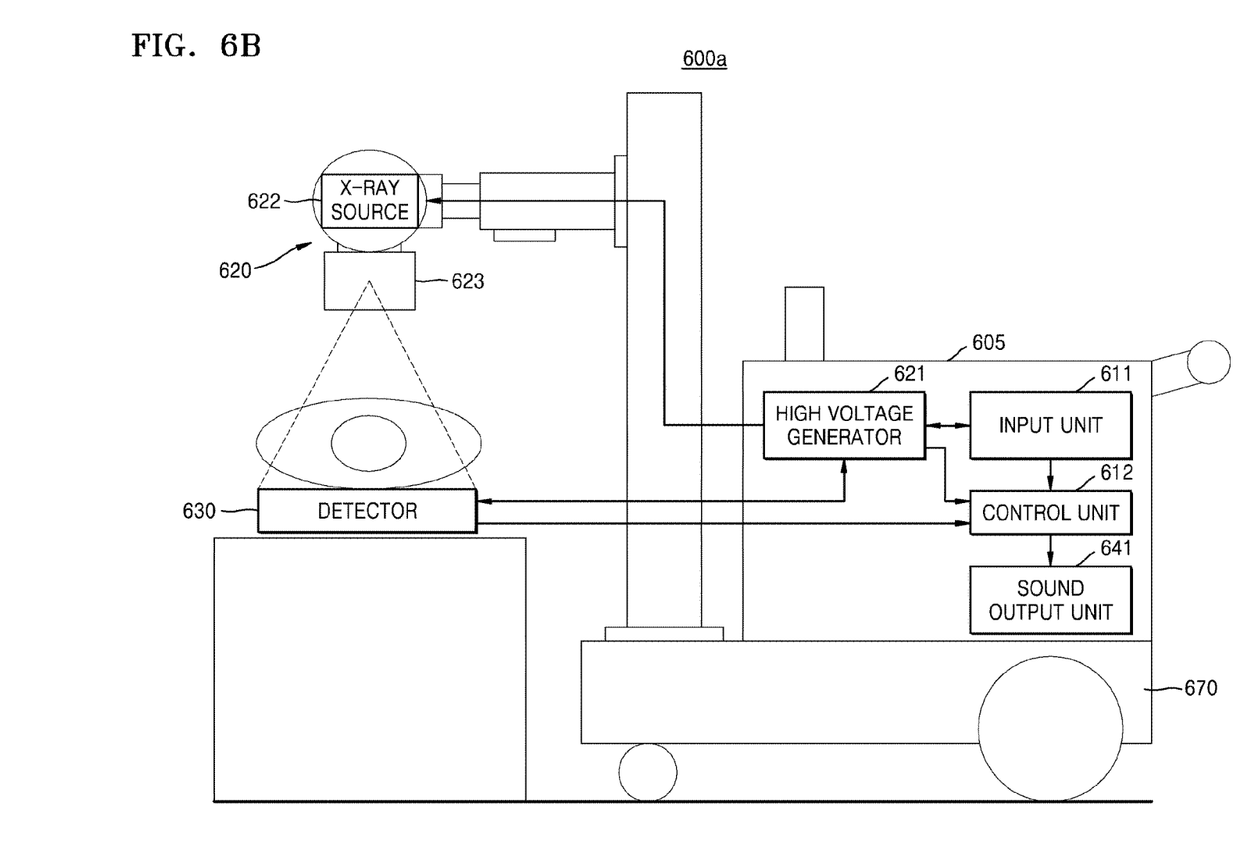
FIG. 6B illustrates a construction of a mobile X-ray apparatus, according to an exemplary embodiment.

FIG. 6B illustrates an mobile X-ray apparatus 600a. The mobile X-ray apparatus 600a shown in FIG. 6B includes a transport unit 670 that includes a wheel for transporting the X-ray apparatus 600a, a main unit 605 that includes an input unit 611 via which commands for operating the X-ray apparatus 600a are input, a high voltage generator 621 which is configured for generating a high voltage applied to an X-ray source 622, a sound output unit 641 which is configured for outputting sound representing information relating to a photographing operation such as an X-ray irradiation, and a control unit 612 which is configured for controlling overall operations of the X-ray apparatus 600a, an X-ray irradiation unit 620 which includes the X-ray source 622 configured for generating the X-ray, and a collimator 623 configured for guiding a path of the X-ray generated and emitted from the X-ray source 622, and a detector 630 configured for detecting the X-ray irradiated from the X-ray irradiation unit 620 and which has propagated through an object.

The input unit 611, the high voltage generator 621, the sound output unit 641, the control unit 612, the X-ray irradiation unit 620 including the X-ray source 622 and the collimator 623, and the detector 630 may respectively correspond to the input unit 111, the high voltage generator 121, the sound output unit 141, the control unit 112, the X-ray irradiation unit 120 including the X-ray source 122 and the collimator 123, and the detector 130. The workstation 450 shown in FIG. 4 may be included in a main unit 605 including the control unit 612.

Figure 7:
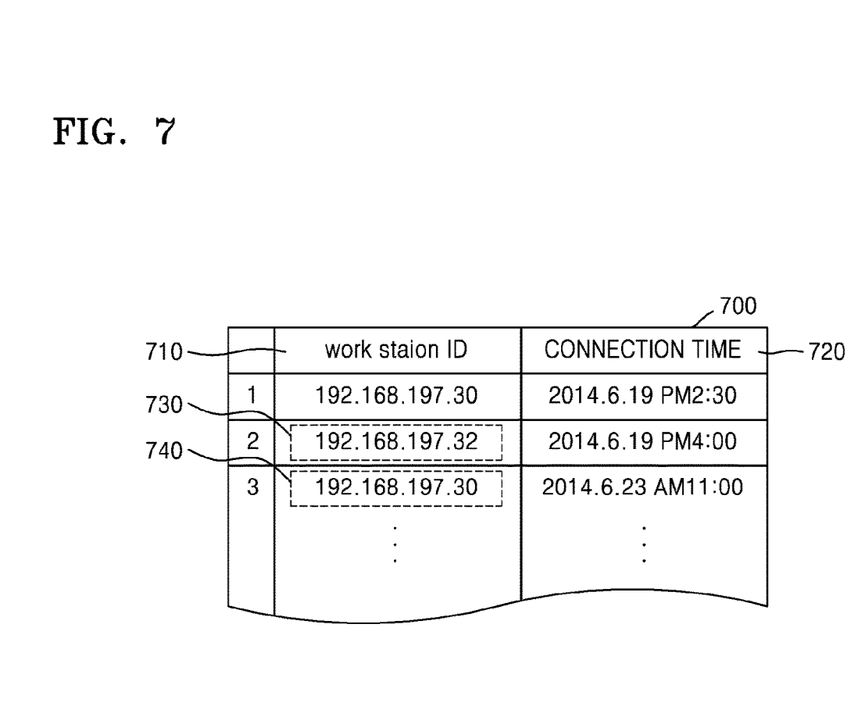
FIG. 7 illustrates an example of connection history information stored in an X-ray detector, according to an exemplary embodiment.

FIG. 7 illustrates an example of connection history information 700 stored in an X-ray detector (not shown), according to an exemplary embodiment.

The connection history information 700, which includes information that relates to the history of connections of a workstation (not shown) to the X-ray detector, may be stored in the memory 330 described above with reference to FIG. 3. Furthermore, the processor 320 shown in FIG. 3 may configure the workstation based on ID information 710 of the workstation and the connection history information 700.

The connection history information 700 may include pieces of ID information 710 of at least one workstation that was previously connected to the X-ray detector and pieces of time information 720 indicating times and dates when the workstation was previously connected to the X-ray detector.

FIG. 7 illustrates an example where the ID information 710 of the workstation includes an IP address according to an exemplary embodiment. FIG. 7 shows that a workstation having an IP address 730 of 192.168.197.32 connected to an X-ray detector on Jun. 19, 2014, at 4:00 PM. Furthermore, as shown in FIG. 7, a workstation having an IP address 740 of 192.168.197.30 initially connected to the X-ray detector on Jun. 19, 2014, at 2:30 PM, and thereafter on Jun. 23, 2014, at 11:00 AM.

The X-ray detector may find ID information of the last workstation that connected to the X-ray detector based on the pieces of time information 720 contained in the connection history information 700.

According to an exemplary embodiment, the X-ray detector may perform a configuration of a workstation based on ID information of the workstation and the connection history information 700.

The X-ray detector may use the connection history information 700 to determine whether a workstation (i.e., a central control unit) that transmits ID information (e.g., an SSID) is identical to the last workstation that connected to the X-ray detector.

If the X-ray detector determines that the workstation (central control unit) transmitting the ID information (the SSID) is different from the last workstation that connected to the X-ray detector, the X-ray detector may change its SSID to be the same as the SSID of the workstation (i.e., the current central control unit).

If the SSID of the X-ray detector is set to the same as the SSID of the workstation (central control unit), the X-ray detector and the workstation (central control unit) may automatically connect to each other. Thereafter, the X-ray detector may wirelessly transmit or receive data to or from the workstation (central control unit).

According to an exemplary embodiment, the X-ray detector may use ID information received from a workstation (central control unit) and the connection history information 700 to determine if configuration data used for the configuration of the workstation (central control unit) (hereinafter, having the same meaning as 'configuration data for the workstation (central control unit)') is identical to configuration data used for the configuration performed by the X-ray detector.

By using the connection history information 700 indicating a history of connections of a workstation (central control unit) to the X-ray detector and information that relates to a version of configuration data used for a configuration performed by the X-ray detector, the X-ray detector may compare configuration data for the workstation (central control unit) with configuration data for the X-ray detector. A process of comparing configuration data for a workstation (central control unit) with configuration data for an X-ray detector will now be described in more detail with reference to FIG. 7.

Referring to FIG. 7, the workstation having the IP address 740 of 192.168.197.30 connected to the X-ray detector on Jun. 19, 2014, at 2:30 PM.

Based on the IP address 740 of 192.168.197.30 of the workstation and the connection history information 700, the X-ray detector may determine that the workstation having the IP address 740 of 192.168.197.30 (hereinafter, referred to as the 'workstation A') had not connected to the X-ray detector before Jun. 19, 2014, at 2:30 PM.

Thus, when the workstation A that had not been connected to the X-ray detector attempted to wirelessly connect to the X-ray detector on Jun. 19, 2014, at 2:30 PM, the X-ray detector may determine that the configuration data used for configuration of the workstation A is different from the configuration data used for the configuration performed by the X-ray detector.

In order to change the configuration data for the workstation A to be the same as the configuration data for the X-ray detector, the X-ray detector may transmit the configuration data for the X-ray detector to the workstation A.

In addition, FIG. 7 shows that the workstation A initially connected to the X-ray detector on Jun. 19, 2014, at 2:30 PM, and thereafter on Jun. 23, 2014, 11:00 AM.

According to an exemplary embodiment, it is assumed herein that configuration data for the X-ray detector was updated between Jun. 19, 2014, at 2:30 PM, and Jun. 23, 2014, at 11:30 AM, e.g., on Jun. 20, 2014, at 7:00 PM.

If the workstation A wirelessly connected to the X-ray detector for the second time on Jun. 23, 2014, at 11:00 AM after the configuration data for the X-ray detector was updated, the X-ray detector may determine that configuration data for the workstation A is different from configuration data for the X-ray detector based on the connection history information 700 and an updated history. Thus, the X-ray detector may transmit the updated configuration data to the workstation A. In this aspect, the X-ray detector may perform a configuration of the workstation A automatically by transmitting the updated configuration data to the workstation A.

Alternatively, if configuration data for the X-ray detector has not been updated since Jun. 19, 2014, at 2:30 PM, and when the workstation A was connected after the same date and time, the X-ray detector may determine that the configuration data for the workstation A is the same as the configuration data for the X-ray detector. Thus, when the workstation A was connected to the X-ray detector on Jun. 23, 2014, at 11:30 AM, the X-ray detector may immediately complete the configuration of the workstation A without transmitting the configuration data to the workstation A.

According to an exemplary embodiment, for performance of a configuration of an X-ray detector, the X-ray detector does not need to request configuration from a workstation. Instead of making such a request, the X-ray detector may determine if the configuration data for the workstation is the latest data. Thus, each time the X-ray detector connects to a different workstation, the X-ray detector does not need to change its configuration data suitably for a configuration of the workstation. In other words, the X-ray detector may be automatically configured without needing to receive configuration data (e.g., calibration data) from the workstation.

Figure 8:
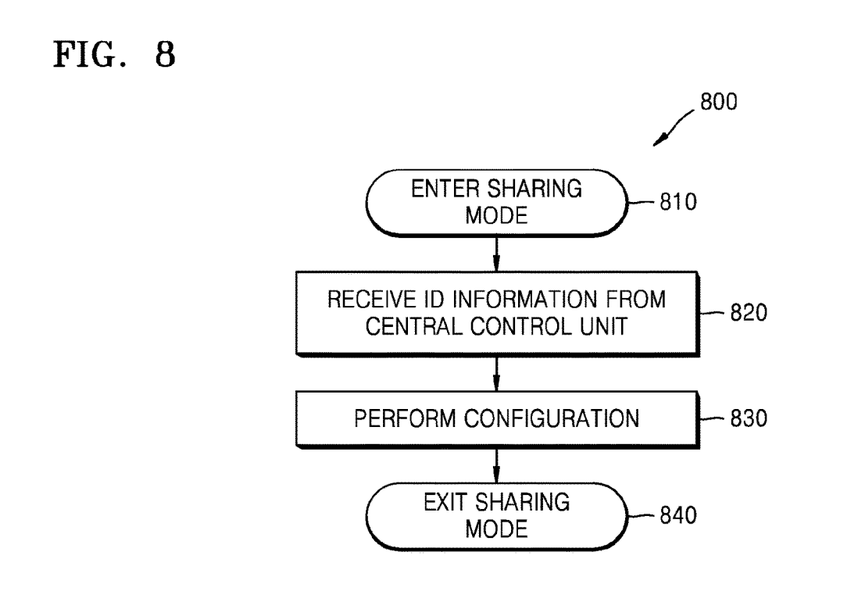
FIG. 8 is a flowchart of a method for using an X-ray detector that is able to connect wirelessly to a central control unit, according to an exemplary embodiment.

FIG. 8 is a flowchart of a method for using an X-ray detector 200 that connects wirelessly to a central control unit, according to an exemplary embodiment.

The method according to the present exemplary embodiment includes the same operations as those performed by the X-ray detector 200 as described above with reference to FIGS. 1 and 2. Thus, in describing the method, the same descriptions as already presented with respect to FIGS. 1 and 2 are omitted.

Referring to FIGS. 1, 2 and 8, first, in operation 810, the X-ray detector 200 enters a sharing mode. Then, in operation 820, the X-ray detector 200 may receive ID information from the central control unit via the data transceiver 210. The X-ray detector 200 may perform a configuration of the X-ray detector based on the ID information via the processor 220 in operation 830. After the X-ray detector 200 completes its configuration, the X-ray detector 200 may exit the sharing mode in operation 840.

Figure 9:
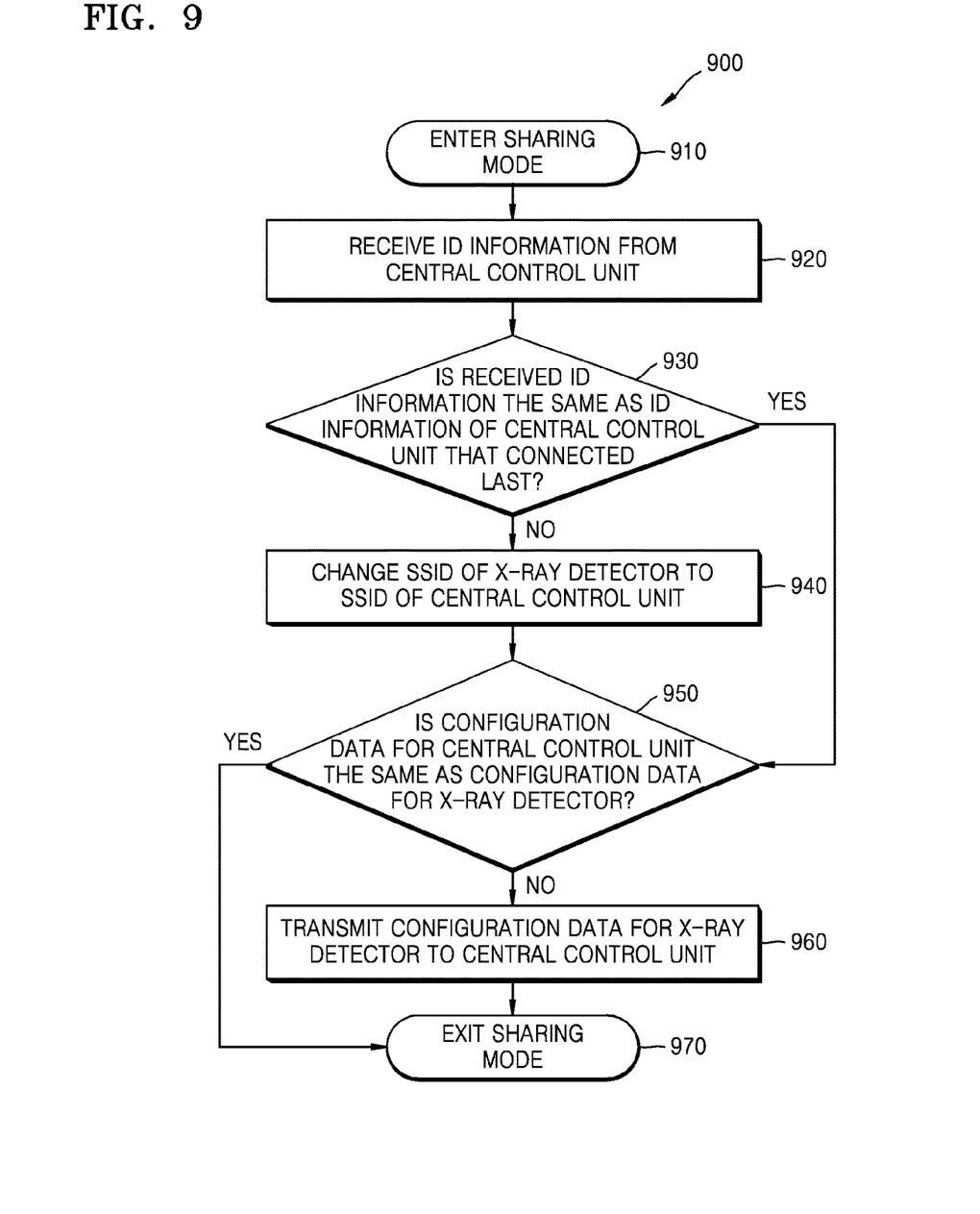
FIG. 9 is a flowchart of a method for using an X-ray detector that is able to connect wirelessly to a central control unit, according to another exemplary embodiment.

FIG. 9 is a flowchart of a method for using an X-ray detector 300 that connects wirelessly to a central control unit, according to another exemplary embodiment.

The method according to the present exemplary embodiment includes the same operations as those performed by the X-ray detector 300 as described above with reference to FIG. 3 Thus, in describing the method, the same descriptions as already presented with respect to FIG. 3 are omitted.

Referring to FIGS. 3 and 9, in operation 910, the X-ray detector 300 enters a sharing mode. Then, in operation 920, the X-ray detector 300 may receive ID information from a central control unit (not shown) via the data transceiver 310.

In operation 930, the processor 320 of the X-ray detector 300 may determine whether the received ID information of the central control unit is the same as ID information of a central control unit to which the X-ray detector 300 connected last.

If the received ID information of the central control unit is different from the ID information of the central control unit to which the X-ray detector 300 connected last, then in operation 940, an SSID of the X-ray detector 300 may be changed to be the same as an SSID of the central control unit.

Otherwise, if the received ID information of the central control unit is the same as the ID information of the central control unit to which the X-ray detector 300 connected last, the processor 320 may skip operation 940 and perform operation 950.

In operation 950, the processor 320 may determine whether configuration data for the central control unit is the same as configuration data for the X-ray detector 300.

If the configuration data for the central control unit is different from the configuration data for the X-ray detector 300, then in operation 960, the X-ray detector 300 may transmit the configuration data for the X-ray detector 300 to the central control unit. After the central control unit completes its configuration by transmitting the configuration data for the X-ray detector 300, the X-ray detector 300 may exit the sharing mode in operation 970.

Otherwise, if the configuration data for the central control unit is the same as the configuration data for the X-ray detector, operation 960 may be skipped, and the X-ray detector 300 may exit the sharing mode.

Figure 10:
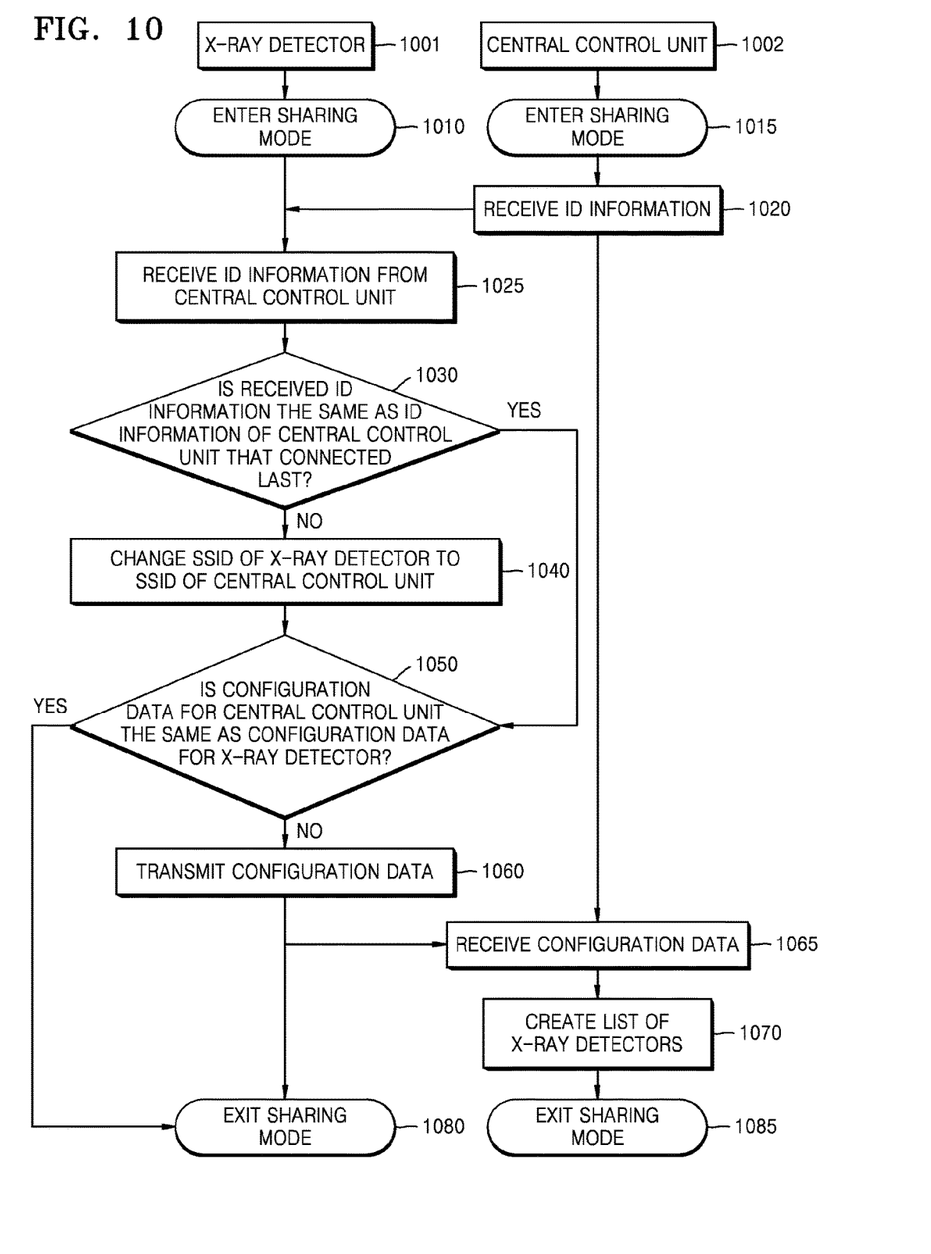
FIG. 10 is a flowchart illustrating a data flow between an X-ray detector and a central control unit, according to an exemplary embodiment.

FIG. 10 is a flowchart illustrating a data flow between an X-ray detector 1001 and a central control unit 1002, according to an exemplary embodiment.

Referring to FIGS. 3 and 10, in operations 1010 and 1015, the X-ray detector 1001 and the central control unit 1002 enter a sharing mode. Then, in operation 1020, the central control unit 1002 may transmit ID information to the X-ray detector 1001. The X-ray detector 1001 may receive the ID information from the central control unit 1002 via the data transceiver 310 in operation 1025.

In operation 1030, the X-ray detector 1001 may determine whether the received ID information is the same as ID information of a central control unit to which the X-ray detector 1001 connected last.

If the received ID information is different from the ID information of the central control unit to which the X-ray detector 300 connected last, then in operation 1040, an SSID of the X-ray detector 1001 may be changed to be the same as an SSID of the central control unit 1002.

Otherwise, if the received ID information is the same as the ID information of the central control unit to which the X-ray detector 300 connected last, operation 1040 may be skipped, and the next operation 1050 may be performed.

In operation 1050, the X-ray detector 1001 may determine whether configuration data for the central control unit 1002 is the same as configuration data for the X-ray detector 1001.

If the configuration data for the central control unit 1002 is different from the configuration data for the X-ray detector 1001, in operation 1060, the X-ray detector 1001 may transmit the configuration data for the X-ray detector 1001 to the central control unit 1002. When X-ray detector 1001 completes configuration (by transmitting the configuration data for the X-ray detector 1001 to the central control unit 1002, the X-ray detector 1001 may exit the sharing mode in operation 1080.

Otherwise, if the configuration data for the central control unit 1002 is the same as the configuration data for the X-ray detector 1001, the X-ray detector 1001 may exit the sharing mode by skipping operation 1060 and executing operation 1080.

In operation 1065, the central control unit 1002 may receive the configuration data for the X-ray detector 1001 from the X-ray detector 1001. If the X-ray detector 1001 is a new X-ray detector, in operation 1070, the central control unit 1002 may add the X-ray detector 1001 to a list of X-ray detectors.

When the central control unit 1002 completes its configuration by receiving the configuration data for the X-ray detector 1001, in operation 1085, the central control unit 1002 may exit the sharing mode.

If the configuration data for the central control unit 1002 is the same as the configuration data for the X-ray detector 1001, the central control unit 1002 may exit the sharing mode by skipping operations 1065 and 1070 and executing operation 1085.

The exemplary embodiments may be written as computer programs and may be implemented in general-use digital computers that execute the programs using a non-transitory computer-readable recording medium.

Examples of the non-transitory computer-readable recording medium include magnetic storage media (e.g., ROM, floppy disks, hard disks, etc.), optical recording media (e.g., CD-ROMs or DVDs), etc.

While one or more exemplary embodiments have been described with reference to the figures, it will be understood by those of ordinary skill in the art that various changes in form and details may be made therein without departing from the spirit and essential characteristics of the present inventive concept as defined by the following claims. Thus, the above-described exemplary embodiments are exemplary in all aspects, and are not intended to limit the scope of the present inventive concept.

What is claimed is:

1. An X-ray detector, comprising:
   a data transceiver configured to wirelessly receive, from a central controller, identification (ID) information that relates to the central controller when the X-ray detector is in a sharing mode in which the X-ray detector exchanges predetermined data with the central controller;
   a memory configured to store connection history information that includes information relating to a history of connections of the central controller to the X-ray detector and X-ray detector configuration data that is to be used for a configuration of the X-ray detector; and
   a processor configured to determine whether configuration data to be used for a configuration of the central controller is the same as configuration data used for a configuration performed by the processor based on the ID information and the connection history information,
   wherein when a determination is made that the configuration data to be used for the configuration of the central controller is the same as the configuration data used for the configuration performed by the processor based on the ID information and the connection history information, the processor is further configured to perform the configuration of the central controller based on the received ID information and the stored connection history information, and
   wherein when the configuration data to be used for the configuration of the central controller is determined to be different from the X-ray detector configuration data, the data transceiver is further configured to update the configuration data to be used for the configuration of the central controller by transmitting the stored X-ray detector configuration data to the central controller, and the processor is further configured to perform the configuration of the central controller based on the updated configuration data.

2. The X-ray detector of claim 1, wherein the X-ray detector is configured to automatically connect to the central controller in a wireless manner.

3. The X-ray detector of claim 1, wherein the processor is further configured to determine, based on the connection history information, whether the central controller that transmits the ID information is identical to a second central controller which connected last to the X-ray detector, and, if the central controller that transmits the ID information is different from the second central controller which connected last to the X-ray detector, to change a service set identifier (SSID) of the X-ray detector to be the same as an SSID of the central controller that transmits the ID information.

4. The X-ray detector of claim 1, wherein the X-ray detector configuration data comprises at least one from among calibration data, a detection parameter, an Internet Protocol (IP) address, a service set identifier (SSID), and a media access control (MAC) address of the X-ray detector.

5. The X-ray detector of claim 1, wherein the connection history information comprises at least one piece of ID information that relates to a central controller that was previously connected to the X-ray detector and at least one piece of time information indicating at least one time when the central controller was previously connected to the X-ray detector.

6. The X-ray detector of claim 1, wherein the ID information comprises at least one from among an Internet Protocol (IP) address, a serial number, a service set identifier (SSID), and a media access control (MAC) address of the central controller.

7. The X-ray detector of claim 1, wherein the ID information is broadcast by the central controller, and the data transceiver is further configured to receive the broadcast ID information.

8. The X-ray detector of claim 1, wherein the X-ray detector is configured to wirelessly connect to the central controller when the X-ray detector is in a sharing mode.

9. The X-ray detector of claim 8, further comprising a user input receiver via which the sharing mode is initiated when a user input is received via the user input receiver.

10. The X-ray detector of claim 8, wherein the sharing mode is initiated when the data transceiver receives a command input via the central controller.

11. The X-ray detector of claim 1, further comprising a display configured to display data being transmitted by the data transceiver and data being received by the data transceiver,
wherein the display is further configured to display a user interface screen that indicates a status of a transmission of configuration data used for the configuration performed by the processor to the central controller.

12. An X-ray image processing system comprising:
the X-ray detector of claim 1; and
a central controller.

13. The system of claim 12, wherein the central controller is located within an X-ray imaging room.

14. The system of claim 12, wherein the central controller is included in a mobile X-ray system.

15. A method for using an X-ray detector, the method comprising:
wirelessly receiving, from a central controller, identification (ID) information that relates to the central controller when the X-ray detector is in a sharing mode in which the X-ray detector exchanges predetermined data with the central controller;
storing connection history information in a memory of the X-ray detector, the connection history information including information that relates to a history of connections of the central controller to the X-ray detector and X-ray detector configuration data that is used for a configuration of the X-ray detector in the memory of the X-ray detector;
determining whether configuration data to be used for a configuration of the central controller is the same as configuration data used for a configuration performed by the X-ray detector based on the ID information and the connection history information; and
when a determination is made that the configuration data to be used for the configuration of the central controller is the same as the configuration data used for the configuration performed by the X-ray detector based on the ID information and die connection history information, performing the configuration of the central controller based on the received ID information and the stored connection history information; and
when the configuration data to be used for the configuration of the central controller is different from the X-ray detector configuration data, update the configuration data to be used for the configuration of the central controller by transmitting the stored X-ray detector configuration data to the central controller, and performing the configuration of the central controller based on the updated configuration data.

16. The method of claim 15, wherein the performing the configuration comprises the X-ray detector automatically connecting to the central controller in a wireless manner.

17. The method of claim 15, wherein the performing the configuration comprises:
determining, based on the connection history information, whether the central controller that transmits the ID information is identical to a second central controller which connected last to the X-ray detector; and
changing a service set identifier (SSID) of the X-ray detector to be the same as an SSID of the central controller that transmits the ID information if the central controller that transmits the ID information is different from the second central controller which connected last to the X-ray detector.

18. The method of claim 15, wherein the X-ray detector configuration data comprises at least one from among calibration data, a detection parameter, an Internet Protocol (IP) address, a service set identifier (SSID), and a media access control (MAC) address of the X-ray detector.

19. The method of claim 15, wherein the connection history information comprises at least one piece of ID information that relates to a central controller that was previously connected to the X-ray detector and at least one piece of time information indicating at least one time when the central controller was previously connected to the X-ray detector.

20. The method of claim 15, wherein the ID information comprises at least one from among an Internet Protocol (IP) address, a serial number, a service set identifier (SSID), and a media access control (MAC) address of the central controller.

21. The method of claim 16, wherein the X-ray detector automatically connecting to the central controller in a wireless manner further comprises the X-ray detector connecting wirelessly to the central controller when the X-ray detector is in a sharing mode.

22. The method of claim 21, wherein the sharing mode is initiated when a user input receiver of the X-ray detector receives a user input.

23. The method of claim 21, wherein the sharing mode is initiated when a data transceiver of the X-ray detector receives a command input via the central controller.

24. The method of claim 15, wherein the performing the configuration comprises displaying a status of a transmission of configuration data used for the configuration performed by the X-ray detector to the central controller.

* * * * *